US010426895B2

(12) United States Patent
Marsh et al.

(10) Patent No.: US 10,426,895 B2
(45) Date of Patent: Oct. 1, 2019

(54) DRIVE MECHANISM AND DRUG DELIVERY DEVICE HEREWITH

(71) Applicant: Sanofi, Paris (FR)

(72) Inventors: William Marsh, Buckinghamshire (GB); Anthony Paul Morris, Coventry (GB); Joseph Butler, Rugby (GB); Matthew Jones, Warwick (GB); Samuel Steel, Warwickshire (GB); Richard James Vincent Avery, Gloucestershire (GB)

(73) Assignee: Sanofi, Paris (FR)

( * ) Notice: Subject to any disclaimer, the term of this patent is extended or adjusted under 35 U.S.C. 154(b) by 243 days.

(21) Appl. No.: 15/517,719

(22) PCT Filed: Oct. 9, 2015

(86) PCT No.: PCT/EP2015/073429
§ 371 (c)(1),
(2) Date: Apr. 7, 2017

(87) PCT Pub. No.: WO2016/055624
PCT Pub. Date: Apr. 14, 2016

(65) Prior Publication Data
US 2017/0312447 A1    Nov. 2, 2017

(30) Foreign Application Priority Data

Oct. 9, 2014    (EP) .................................... 14306591

(51) Int. Cl.
*A61M 5/315*    (2006.01)
*A61M 5/20*    (2006.01)
(Continued)

(52) U.S. Cl.
CPC .......... *A61M 5/31576* (2013.01); *A61M 5/20* (2013.01); *A61M 5/24* (2013.01);
(Continued)

(58) Field of Classification Search
CPC .............. A61M 5/31576; A61M 5/315; A61M 5/31553; A61M 5/31583; A61M 5/31535;
(Continued)

(56) References Cited

U.S. PATENT DOCUMENTS 7,955,303 B2 *  6/2011  Burren ................... A61M 5/24
                                                    604/136
8,267,870 B2 *  9/2012  Freeman .............. A61B 5/1411
                                                    600/573

(Continued)

FOREIGN PATENT DOCUMENTS

DE    10 2005 060929    3/2007
EP       0 730 876      9/1996
(Continued)

OTHER PUBLICATIONS

International Preliminary Report on Patentability in International Application No. PCT/EP2015/073429, dated Apr. 11, 2017, 14 pages.

(Continued)

*Primary Examiner* — Amber R Stiles
*Assistant Examiner* — Nicholas J Chidiac
(74) *Attorney, Agent, or Firm* — Fish & Richardson P.C.

(57) ABSTRACT

The present disclosure relates to a drive mechanism which is suitable for an injection device, especially a pen type drug delivery device and to such a drug delivery device. The mechanism comprises a spring driven rotatable drive member, a rotatable driven member, a clutch rotationally coupling the driven member and the drive member in a coupled state and allowing relative clockwise and anti-clockwise rotation between the driven member and the drive member in a decoupled state, and a spring biasing the clutch into its coupled state and allowing relative axial movement between the drive member and the driven member into the decoupled (Continued)

state of the clutch against the bias of the spring. The clutch comprises a first ring of crown teeth on the drive member and a second ring of corresponding crown teeth on the driven member with each crown tooth having in the clockwise and the anti-clockwise direction different ramped tooth angles such that the teeth are allowed to override each other in the de-coupled state of the clutch with a different resistance in the clockwise and the anti-clockwise direction.

16 Claims, 2 Drawing Sheets

(51) Int. Cl.
A61M 5/31 (2006.01)
A61M 5/24 (2006.01)

(52) U.S. Cl.
CPC ........ *A61M 5/315* (2013.01); *A61M 5/31553* (2013.01); *A61M 5/31583* (2013.01); *A61M 5/31535* (2013.01); *A61M 5/31541* (2013.01); *A61M 2005/3126* (2013.01); *A61M 2205/02* (2013.01)

(58) Field of Classification Search
CPC ...... A61M 5/31541; A61M 5/20; A61M 5/24; A61M 2005/3126; A61M 2205/02
See application file for complete search history.

(56) References Cited

U.S. PATENT DOCUMENTS

2002/0120235 A1* 8/2002 Enggaard ................ A61M 5/20
604/135
2008/0306445 A1* 12/2008 Burren ................... A61M 5/24
604/136

FOREIGN PATENT DOCUMENTS

| WO | WO 2011/003979 | 1/2011 |
| WO | WO 2011/054775 | 5/2011 |
| WO | WO 2012/154110 | 11/2012 |
| WO | WO 2012/156253 | 11/2012 |

OTHER PUBLICATIONS

International Search Report and Written Opinion in International Application No. PCT/EP2015/073429, dated Apr. 18, 2016, 20 pages.

* cited by examiner

DRIVE MECHANISM AND DRUG DELIVERY DEVICE HEREWITH

CROSS-REFERENCE TO RELATED APPLICATIONS

This application is a U.S. national stage application under 35 USC § 371 of International Application No. PCT/EP2015/073429, filed on Oct. 9, 2015, which claims priority to European Patent Application No. 14306591.0, filed on Oct. 9, 2014, the entire contents of which are incorporated herein by reference.

TECHNICAL FIELD

The present disclosure relates to a drive mechanism which is suitable for an injection device, especially a pen type drug delivery device for selecting and dispensing a number of user variable doses of a medicament. Further, the disclosure relates to such a drug delivery device.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some embodiments are directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

SUMMARY

In certain aspects, a drive mechanism comprises a spring driven rotatable drive member, a rotatable driven member, a clutch for rotationally coupling the driven member and the drive member in a coupled state and allowing relative clockwise and anti-clockwise rotation between the driven member and the drive member in a decoupled state, and a (clutch) spring biasing the clutch into its coupled state and allowing relative axial movement between the drive member and the driven member into the decoupled state of the clutch against the bias of the spring.

Preferably, the clutch comprises a first ring of crown teeth on the drive member and a second ring of corresponding crown teeth on the driven member with each crown tooth having in the clockwise and the anti-clockwise direction different ramped tooth angles such that the teeth are allowed to override each other in the de-coupled state of the clutch with a different resistance in the clockwise and the anti-clockwise direction.

Some embodiments may provide a drive mechanism and a drug delivery device with a reliable and repeatable clutch interface.

Creating a reliable and repeatable clutch interface may be achieved by controlling the parameters influencing the torque necessary to overhaul the clutch. In some embodiments, the material of the drive member may be polybutylene terephthalate (PBT) or polyoxymethylene (POM) whereas the material of the rotatable driven member may be PBT, POM or polycarbonate (PC). Preferably, the material of the drive member is PBT and the material of the rotatable driven member is PBT, PC or, preferably, POM. As an alternative, if the material of the drive member is POM, the material of the rotatable driven member is POM or PC. In a further preferred alternative, the material of the drive member is PC and the material of the rotatable driven member is PBT or POM. These materials are suitable for injection molding and in combination, provide a reliable and robust interface for generating a torque necessary to overhaul the clutch in a repeatable manner.

According to a further aspect, the coefficient of friction between the teeth is $0.05 \leq \mu \leq 0.3$, preferably $0.09 \leq \mu \leq 0.11$, for example $\mu=0.1$. According to a further aspect, the teeth have a surface roughness of $0.2 \leq Ra \leq 10$ micrometers, preferably $0.7 \leq Ra \leq 0.9$, for example $Ra=0.8$.

A clutch is a component or feature suitable for connecting two component parts either by form fit (positive fit), e.g. with teeth suitable for engaging and disengaging each other, or by a non-positive (frictional) connection or a combination thereof. Actuation of a clutch, i.e. the act of coupling or decoupling, may include a relative movement of clutch parts or clutch features, for example for disengaging clutch teeth, and/or may include a change in a force exerted on clutch parts or clutch features.

The crown teeth of the clutch are preferably provided as axially extending teeth located at the distal end face of one component part, e.g. the drive member, and the proximal end face of the other component part, e.g. the driven member. However, it is also possible to provide crown teeth in a recess or on a flange.

In a preferred embodiment, the drive mechanism further comprises a torsion spring which is directly or indirectly coupled to the drive member such that rotation of the drive member in a first rotational direction charges (strains) the spring and that rotation of the drive member in a second, opposite rotational direction discharges (releases) the spring. To reduce the torque necessary to overhaul the clutch during dose setting, while preventing unintended discharging of the torsion spring, the teeth may have a steeper ramped tooth angle in the second rotational direction and have a shallower ramped tooth angle in the first rotational direction. In addition, or as an alternative, the teeth may have a higher friction coefficient in the second rotational direction and have a lower friction coefficient in the first rotational direction.

The drive member may be a separate component part which is rotationally constrained to a dose setting member, e.g. a number sleeve or a dose selector. The drive member may be rotatable and axially constrained, e.g. to a housing, or may be rotatable along a helical path. The driven member may be a tubular element located e.g. inside the number sleeve. On the other hand, the driven member may drive a further component part, for example a piston rod.

A drug delivery device for selecting and dispensing a number of user variable doses of a medicament preferably comprises a drive mechanism as defined above and further a housing, a dose setting member located within the housing, and a piston rod engaging the driven member, wherein the drive member is operatively interposed between the driven member and the dose setting member. In this embodiment the drive member may act as a clutch element for coupling and decoupling the driven member and the dose setting member, e.g. to allow relative rotation during dose setting (or dose correcting) and to prevent relative rotation during dose dispensing.

The drug delivery device may further comprise a second clutch for rotationally coupling and decoupling the driven member and the housing. Preferably, the driven member is axially displaceable relative to the housing between a first position in which the second clutch rotationally couples the driven member and the housing and a second position in which the second clutch rotationally decouples the driven member from the housing. In other words, the drug delivery device may be switched between a dose setting (or correcting) state in which rotation of the driven member is prevented and a dose dispensing state in which rotation of the driven member is allowed by axial movement of the driven member. In this respect, a button may be provided acting directly or indirectly on the driven member for axial displacement, e.g. against the bias of the clutch spring.

When switching between the dose setting (or correcting) state and the dose dispensing state it is desirable to avoid uncontrolled movement of the driven member, especially in embodiments where the driven member is coupled to a piston rod or the like effecting dose dispensing. Such uncontrolled movement of the driven member could result in amending the set dose prior to dispensing, i.e. underdosage or overdosage. To avoid uncontrolled movement of the driven member the teeth of the clutch are preferably in a coupled state when the driven member and the housing are decoupled by the second clutch. Further, the driven member and the housing are preferably coupled by the second clutch when the teeth of the clutch are in a decoupled state. In other words, the driven member is permanently coupled to at least one of the drive member and the housing.

Further, the drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ, and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Non-limiting, exemplary embodiments will now be described with reference to the accompanying drawings, in which.

DETAILED DESCRIPTION

Figure 1:
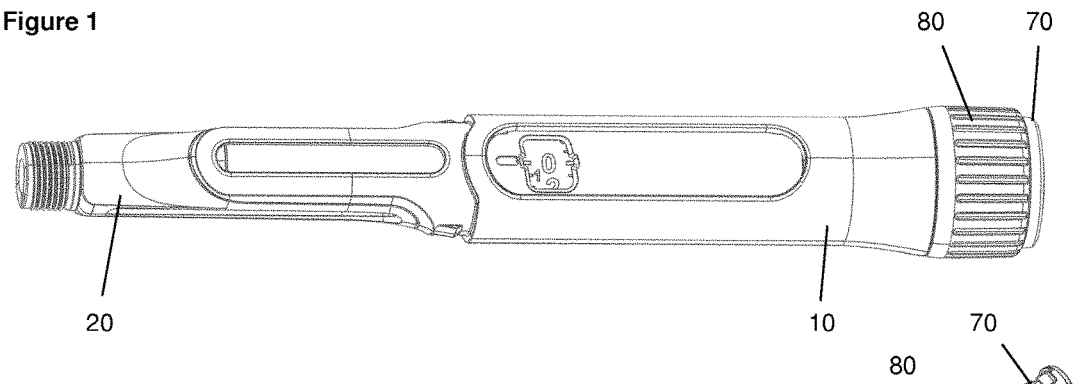
FIG. 1 shows a top view of a drug delivery device.
Figure 2:
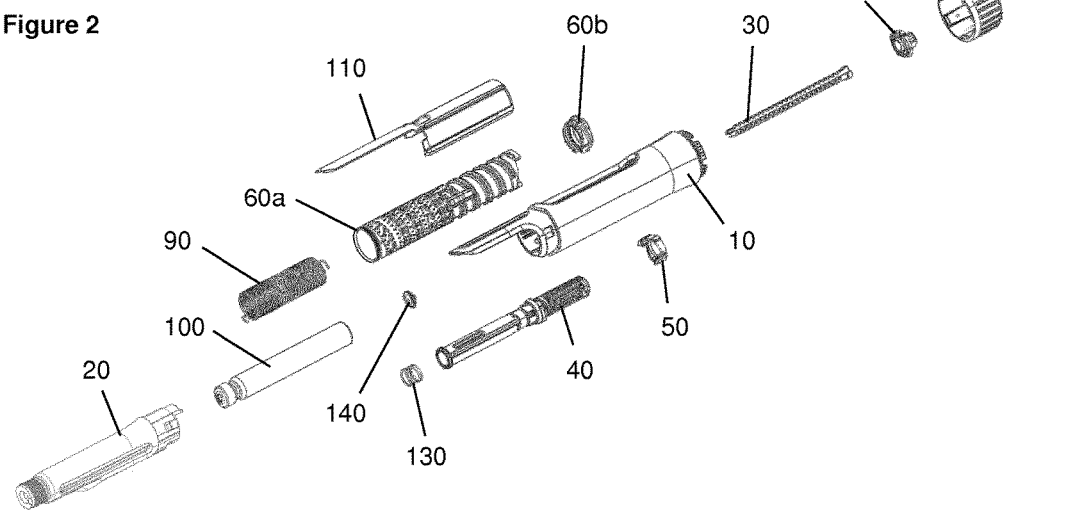
FIG. 2 shows an exploded view of the components of the device of FIG. 1.
Figure 3:
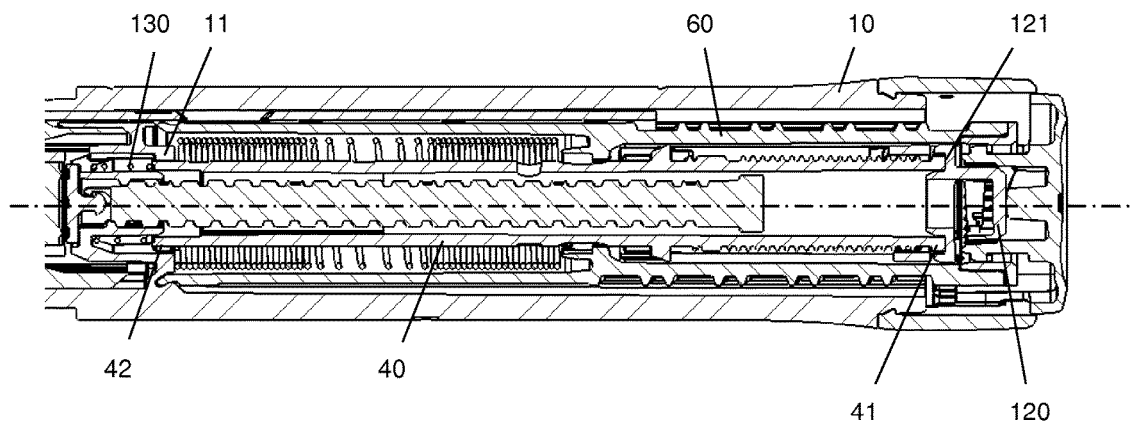
FIG. 3 shows a sectional view of the proximal end of the device of FIG. 1.
Figure 4:
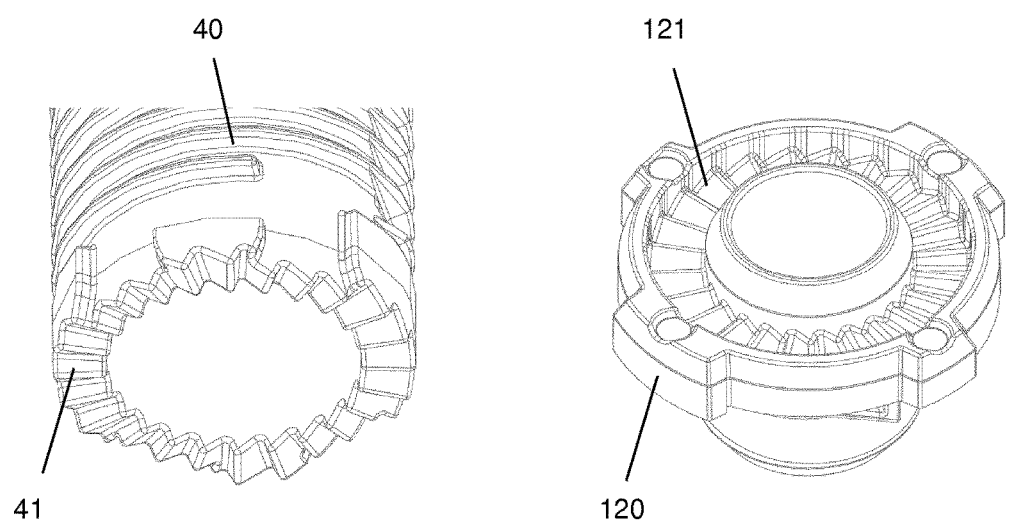
FIG. 4 shows a detail of the driven member and the drive member of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

As will be explained in more detail below, the clutch plate 120 is a spring driven rotatable drive member driving the drive sleeve 40 during dose dispensing to rotate relative to the housing 10 to thereby advance piston rod 30. The clutch plate 120 is in turn driven by the number sleeve 60 to which it is rotationally constrained which is attached to one end of the torsion spring 90. Although driving the piston rod 30 during dose dispensing, the drive sleeve is considered a driven member because it is driven by the clutch plate 120 (and the number sleeve 60 and the torsion spring 90) during dose dispensing.

The housing 10 or body is a generally tubular element having a proximal end with an enlarged diameter. The housing 10 provides location for the liquid medication cartridge 100 and cartridge holder 20, windows for viewing the dose number on the number sleeve 60 and the gauge element 110, and a feature on its external surface, e.g. a circumferential groove, to axially retain the dose selector 80. An insert comprises an inner thread engaging the piston rod 30. The housing 10 further has at least one internal, axially orientated slot or the like, for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device. The drive spring 90 is attached with one end to the housing 10.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert of housing 10. The lead screw 30 is an elongate member with an outer thread engaging the corresponding thread of the insert of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130. At least one longitudinal spline of the driver 40 engages a corresponding track of the lead screw 30.

The clutch interface between the drive sleeve 40 and the clutch plate 120 comprises a ring of crown teeth 41 located on the proximal end face of the drive sleeve 40 and a ring of corresponding crown teeth 121 located on the distal end face of the clutch plate 120.

It may be beneficial to increase the slipping torque (the torque at which the clutch 41, 121 slips) in one direction relative to the other. For example, this allows the clutch 41, 121 to resist the torque applied by the torsion spring 90. The slipping torque can be increased by increasing the ramp angle, so the teeth 41, 121 contacting in one direction are steeper than in the other and/or increasing the surface roughness of the teeth 41, 121, so the teeth contacting in one direction are rougher than in the other. Alternatively, it may be beneficial to retain the same geometry for a range of devices but to change the slipping torque for each device. This might be achieved by changing the materials for different devices and/or changing the surface roughness for different devices and/or adding lubricant. Typical materials for the clutch interface 41, 121 are summarized in the table below. The first part may be the drive sleeve 40 and the second part may be the clutch plate 120, or vice versa:

| First part | Second part |
|---|---|
| PBT | POM |
| PBT | PC |
| PBT | PBT |
| POM | POM (with additives to change slip properties) |
| POM | PC |

The preferred combination is PBT for the drive sleeve 40 and POM for the clutch plate 120. A preferred coefficient of friction is µ=0.1 and a preferred surface roughness is Ra=0.8.

A splined tooth interface 11, 42 with the housing 10 prevents rotation of the drive sleeve 40 during dose setting. This interface comprises a ring of radially extending outer teeth 42 at the distal end of drive sleeve 40 and corresponding radially extending inner teeth 11 of the housing component 10. When the button 70 is pressed, the drive sleeve teeth 40 and the housing teeth 11 are disengaged from each other allowing the drive sleeve 40 to rotate relative to housing 10. A further splined tooth interface with the number sleeve 60 is not engaged during dialing, but engages when the button 70 is pressed, preventing relative rotation between the drive sleeve 40 and number sleeve 60 during dose dispensing. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

The driver 40 has a threaded section providing a helical track for the nut 50, i.e. a thread. In addition, a last dose abutment or stop is provided which may be the end of the thread track or preferably a rotational hard stop for interaction with a corresponding last dose stop of nut 50, thus limiting movement of the nut 50 on the driver thread.

A further interface of the drive sleeve 40 comprises a ring of ratchet teeth 42 located at the proximal end face of drive sleeve 40 and a ring of corresponding ratchet teeth on the clutch plate 120.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. When a dose is set corresponding to the remaining dispensable amount of medicament in the cartridge 100, a last dose stop is provided on the nut 50 and on the drive sleeve 40, which is engaged with the nut 50.

The dose indicator or number sleeve 60 is a tubular element. The number sleeve 60 is rotated by a torsion spring 90 during dose setting (via dose selector 80) and dose correction and during dose dispensing. The number sleeve 60 is axially constrained to the housing 10, e.g. by snap engagement of a bead on an inner housing surface with a groove on an outer number sleeve surface, while being free to rotate relative to the housing 10. The drive spring 90 is attached with one end to the number sleeve 60. Further, the number sleeve 60 is in threaded engagement with the gauge element 110 such that rotation of the number sleeve causes axial displacement of the gauge element 110. With gauge element 110, the number sleeve 60 defines a zero position ('at rest') and a maximum dose position. Thus, the number sleeve 60 may be seen as a dose setting member. The number sleeve 60 comprises a number sleeve lower 60a which is rigidly fixed to a number sleeve upper 60b during assembly, e.g. by snap engagement, to form the number sleeve 60.

Clutch features which have the form of a ring of splines are provided inwardly, directed on number sleeve upper 60b for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline. Further, number sleeve lower 60a comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60b. Thus, it is also splined via splines to the number sleeve upper 60b when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80)

during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60a. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via the ratchet clutch interface 41, 121. The ratchet clutch 41, 121 provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of the window area which cover the numbers printed on the number sleeve 60 adjacent to the dialed dose to ensure only the set dose number is made visible to the user.

A specific feature of some embodiments is the inclusion of a visual feedback feature in addition to the discrete dose number display typical on devices of this type. The distal end of the gauge element 110 creates a sliding scale through the window in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose. This feature gives clear feedback to the user regarding the approximate size of the dose. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose setting and dispensing.

The drive sleeve 40 is prevented from rotating as the dose is set and the number sleeve 60 rotated, due to the engagement of its splined teeth 42 with teeth 11 of the housing 10. Relative rotation must therefore occur between the clutch plate 120 and drive sleeve 40 via the ratchet clutch interface 41, 121.

The user torque required to rotate the dose selector 80 is a sum of the torque required to wind up the torsion spring 90, and the torque required to overhaul the ratchet clutch interface 41, 121. The clutch spring 130 is designed to provide an axial force to the ratchet clutch interface 41, 121 and to bias the clutch plate 120 onto the drive sleeve 40. This axial load acts to maintain the teeth engagement of the clutch plate 120 and drive sleeve 40. The torque required to overhaul the ratchet clutch 41, 121 in the dose set direction is a function of the axial load applied by the clutch spring 130, the clockwise ramp angle of the ratchet teeth 41, 121, the friction coefficient between the mating surfaces and the mean radius of the ratchet clutch interface 41, 121.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet clutch interface 41, 121 between the clutch plate 120 and the drive sleeve 40. The torque necessary to overhaul the ratchet clutch 41, 121 in the anti-clockwise direction is a function of the axial load applied by the clutch spring 130, the anti-clockwise ramp angle of the ratchet 41, 121, the friction coefficient between the mating surfaces and the mean radius of the ratchet clutch features 41, 121. The torque necessary to overhaul the ratchet clutch 41, 121 must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet clutch interface 41, 121 between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet clutch 41, 121 in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect (correct) any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 41, 121 between the clutch plate 120 and drive sleeve 40 in the anti-clockwise direction. When the ratchet clutch 41, 121 is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts to any axial abuse loads applied by the user, reducing the risk of damaging internal components.

The clutch plate 120 and drive sleeve 40 travel axially with the button 70. This engages the splined tooth interface 41, 121 between the drive sleeve 40 and number sleeve 60, preventing relative rotation between the drive sleeve 40 and number sleeve 60 during dispense. The splined tooth interface 11, 42 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth 11, 42 between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

The clutch interface 41, 121 may be included in any pen injector that requires a rotational clutch. It creates a reliable and repeatable clutch interface, allowing a defined slipping torque in both directions.

| Reference Numerals: | |
|---|---|
| 10 | housing (casing) |
| 11 | spline tooth |
| 20 | cartridge holder |
| 30 | piston rod (lead screw) |
| 40 | drive sleeve |
| 41 | crown tooth |
| 42 | spline tooth |
| 50 | nut |
| 60 | dose setting element |
| 60a | number sleeve lower |
| 60b | number sleeve upper |
| 70 | button |
| 80 | dose selector |
| 90 | torsion spring |
| 100 | cartridge |
| 110 | gauge element |
| 120 | clutch plate |
| 121 | crown tooth |
| 130 | clutch spring |
| 140 | bearing |

The invention claimed is:

1. A drive mechanism for a drug delivery device, the mechanism comprising a spring driven rotatable drive member, a rotatable driven member, a clutch rotationally coupling the driven member and the drive member into a coupled state and allowing relative clockwise and anti-clockwise rotation between the driven member and the drive member when in a decoupled state, and a spring biasing the clutch into the coupled state and allowing relative axial movement between the drive member and the driven member into the decoupled state of the clutch against the bias of the spring, wherein the clutch comprises a first ring of crown teeth on the drive member and a second ring of corresponding crown teeth on the driven member with each crown tooth having in the clockwise and the anti-clockwise direction different ramped tooth angles such that the teeth are allowed to override each other in the de-coupled state of the clutch with a different resistance in the clockwise and the anti-clockwise direction, wherein the drive member is formed of polybutylene terephthalate (PBT), polyoxymethylene (POM), or polycarbonate (PC) and the rotatable driven member is formed of PBT, POM or PC, and a coefficient of friction ($\mu$) between the teeth on the drive member and the teeth on the driven member is between 0.05 and 0.3, and the teeth on the drive member and the teeth on the driven member have a surface roughness (Ra) of $0.2 \leq Ra \leq 10$ micrometers.

2. The drive mechanism according to claim 1, wherein the drive member is formed of PBT and the rotatable driven member is formed of PBT, POM or PC.

3. The drive mechanism according to claim 1, wherein the drive member is formed of POM and the rotatable driven member is formed of POM or PC or wherein the material of the drive member is PC and the material of the rotatable driven member is PBT, or POM.

4. The drive mechanism according to claim 1, wherein the drive member is formed of PC and the rotatable driven member is formed of PBT or POM.

5. The drive mechanism according to claim 1, wherein the coefficient of friction ($\mu$) between the teeth is between 0.09 and 0.11.

6. The drive mechanism according to claim 1, wherein the teeth have a surface roughness (Ra) between 0.7 and 0.9.

7. The drive mechanism according claim 1, wherein the drive member is a separate component part which is rotationally constrained to a dose setting member.

8. The drive mechanism according to claim 1, further comprising a torsion spring which is directly or indirectly coupled to the drive member such that rotation of the drive member in a first rotational direction charges the spring and rotation of the drive member in a second, opposite rotational direction discharges the spring.

9. The drive mechanism according to claim 8, wherein the teeth have a steeper ramped tooth angle in the second rotational direction and have a shallower ramped tooth angle in the first rotational direction.

10. The drive mechanism according to claim 8, wherein the teeth have a higher friction coefficient in the second rotational direction and have a lower friction coefficient in the first rotational direction.

11. A drug delivery device for selecting and dispensing a number of user variable doses of a medicament, the drug delivery device comprising:
a drive mechanism comprising a spring driven rotatable drive member, a rotatable driven member, a clutch rotationally coupling the driven member and the drive member into a coupled state and allowing relative clockwise and anti-clockwise rotation between the driven member and the drive member when in a decoupled state, and a spring biasing the clutch into the coupled state and allowing relative axial movement between the drive member and the driven member into the decoupled state of the clutch against the bias of the spring, wherein the clutch comprises a first ring of crown teeth on the drive member and a second ring of corresponding crown teeth on the driven member with each crown tooth having in the clockwise and the anti-clockwise direction different ramped tooth angles such that the teeth are allowed to override each other in the de-coupled state of the clutch with a different resistance in the clockwise and the anti-clockwise direction, wherein the drive member is formed of polybutylene terephthalate (PBT), polyoxymethylene (POM), or polycarbonate (PC) and the rotatable driven member is formed of PBT, POM or PC, and a coefficient of friction ($\mu$) between the teeth on the drive member and the teeth on the driven member is between 0.05 and 0.3, and the teeth on the drive member and the teeth on the driven member have a surface roughness (Ra) of $0.2 \leq Ra \leq 10$ micrometers,
a housing,
a dose setting member located within the housing, and
a piston rod engaging the driven member,
wherein the drive member is operatively interposed between the driven member and the dose setting member.

12. The drug delivery device according to claim 11, further comprising a cartridge containing a medicament.

13. The drug delivery device according to claim 11, further comprising a second clutch for rotationally coupling and decoupling the driven member and the housing.

14. The drug delivery device according to claim 13, wherein the driven member is axially displaceable relative to the housing between a first position in which the second clutch rotationally couples the driven member and the housing and a second position in which the second clutch rotationally decouples the driven member from the housing.

15. The drug delivery device according to claim 13, wherein the teeth of the clutch are in the coupled state when the driven member and the housing are decoupled by the second clutch.

16. The drug delivery device according to claim 13, wherein the driven member and the housing are coupled by the second clutch when the teeth of the clutch are in the decoupled state.

* * * * *

UNITED STATES PATENT AND TRADEMARK OFFICE
CERTIFICATE OF CORRECTION

PATENT NO. : 10,426,895 B2
APPLICATION NO. : 15/517719
DATED : October 1, 2019
INVENTOR(S) : William Geoffrey Arthur Marsh et al.

Page 1 of 1

It is certified that error appears in the above-identified patent and that said Letters Patent is hereby corrected as shown below:

In the Claims

Column 16, Line 15, Claim 7, after "according", insert -- to --

Signed and Sealed this
Fourth Day of February, 2020

Andrei Iancu
*Director of the United States Patent and Trademark Office*